United States Patent [19]
Russell et al.

[11] Patent Number: 6,140,075
[45] Date of Patent: Oct. 31, 2000

[54] METHOD FOR PRODUCING ANTIBODIES AND PROTEIN TOXINS IN PLANT CELLS

[75] Inventors: David R. Russell, Madison; James T. Fuller, Oregon; Michael J. Miller, Cross Plains, all of Wis.

[73] Assignee: Monsanto Company, St. Louis, Mo.

[21] Appl. No.: 08/902,486

[22] Filed: Jul. 29, 1997

Related U.S. Application Data

[63] Continuation-in-part of application No. 08/279,772, Jul. 25, 1994.

[51] Int. Cl.$^7$ ............................ C12N 15/29; C12N 15/81; C12N 15/00
[52] U.S. Cl. ...................... 435/69.1; 435/320.1; 435/419; 435/468; 536/24.1; 536/23.6; 536/23.5
[58] Field of Search ................................ 435/172.3, 69.1, 435/320.1, 419, 468; 526/23.6, 24.1, 23.5; 800/205, 278, 295, 298

[56] References Cited

U.S. PATENT DOCUMENTS

| | | |
|---|---|---|
| 4,816,397 | 3/1989 | Boss et al. . |
| 4,816,567 | 3/1989 | Cabilly et al. . |
| 4,940,840 | 7/1990 | Suslow et al. . |
| 4,956,282 | 9/1990 | Goodman et al. ................... 435/69.51 |
| 5,102,796 | 4/1992 | Hall et al. . |
| 5,202,422 | 4/1993 | Hiatt et al. . |

FOREIGN PATENT DOCUMENTS

| | | |
|---|---|---|
| 449 375 A2 | 10/1991 | European Pat. Off. . |
| 449 376 A2 | 10/1991 | European Pat. Off. . |
| WO 94/02913 | 8/1984 | WIPO . |
| WO 90/02484 | 3/1990 | WIPO . |
| WO 90/02804 | 3/1990 | WIPO . |
| WO 91/02066 | 2/1991 | WIPO . |
| WO 91/06320 | 5/1991 | WIPO . |
| WO 91/13993 | 9/1991 | WIPO . |
| WO 92/01042 | 1/1992 | WIPO . |

OTHER PUBLICATIONS

Hein et al. Biotechnol. Pro. 1991, vol. 7, pp.455–461, 1991.
Hiatt et al. FEBS Letters. Jul. 1992, vol. 307, pp. 71–75.
Fell et al. The Journal of Biological Chemistry. Aug. 1992, vol. 267, No. 22, pp. 1552–1558.
De Loose et al. Gene. 1991, vol. 99, pp. 95–100.
Chaudhary et al. Nature. vol. 339, pp. 364–366, Jun. 1, 1989.
U.S.Ser. No. 07/851,429 Pang et al.
Benvenuto, et al., "[Phytoantibodies]: a general vector for the expression of immunoglobulin domains in transgenic plants," *Plant Molecular Biology*, 17:865–874 (1991).
Bird, et al., "Single–Chain Antigen–Binding Proteins," *Science*, 242:423–426 (1988).
Chrispeels, M.J., "Sorting of Proteins in the Secretory System," *Annu. Rev. Plant. Physiol. Plant Mol. Biol.*, 42:21–53 (1991).
Denecke, et al., "Protein Secretion in Plant Cells Can Occur via a Default Pathway," *The Plant Cell*, 2:51–59 (1990).
During, et al., "Synthesis and self–assembly of a functional monoclonal antibody in transgenic *Nicotiana tabacum*," *Plant Molecular Biology*, 15:281–293 (1990).
Firek, et al., "Secretion of a functional single–chain Fv protein in transgenic tobacco plants and cell suspension cultures," *Plant Molecular Biology*, 23:861–870 (1993).
Hein, et al., "Evaluation of Immunoglobulins from Plant Cells," *Biotechnol. Prog.*, 7:455–461 (1991).
Hiatt, et al., "Production of antibodies in transgenic plants," *letters to Nature*, 342:76–78 (1989).
Hiatt, A., "Antibodies produced in plants," *Nature*, 344:469–470 (1990).
Hiatt, A.C., "Production of Monoclonal Antibody in Plants," *Transplantation Proceedings*, 23:147–151 (1991).
Hiatt, Andrew C., "Monoclonal antibodies, hybridoma technology and heterologous productions systems," *Current Opinion in Immunology*, 3:229–232 (1991).
Hiatt, et al., "Monoclonal antibody engineering in plants," *FEBS*, 307:71–75 (1992).
Hunt, et al., "The Signal Peptide of aj Vacuolar Protein is Necessary and Sufficient for the Efficient Secretion of a Cytosolic Protein," *Plant Physiol.*, 96:18–25 (1991).
Lund, et al., "A plant signal sequence enhances the secretion of bacterial ChiA in transgenic tobacco," *Plant Molecular Biology*, 18:47–53 (1992).
Owen, et al., "The Expression of Antibodies in Plants," *Chemistry and Industry*, pp. 406–408 (Jun. 1, 1992).
Owen, et al., "Synthesis of a Functional Anti–Phytochrome Single–Chain Fv Protein in Transgenic Tobacco," *Bio/Technology*, 10:790–794 (1992).
Pang, et al., "Use of the signal peptide of *Pisum* vicilin to translocate β–glucuronidase in *Nicotiana tabacum*," *Gene*, 112:229–234 (1992).
Sijmons, et al., "Production of Correctly Processed Human Serum Albumin in Transgenic Plants," *Bio–Technology*, 8:217–223 (1990).
Swain, W., "Antibodies in Plants," *Tibtech*, 9:107–109 (1991).
Tavladoraki, et al., "Transgenic plants expressing a functional single–chain Fv antibody are specifically protected from virus attack," *Nature*, 366:469–472 (1993).

*Primary Examiner*—Lynette R. F. Smith
*Assistant Examiner*—Thomas Haas
*Attorney, Agent, or Firm*—McKenna & Cuneo, LLP

[57] ABSTRACT

A method for producing antibodies and plant protein toxins in plant cells is described which includes the steps of providing a genetic construct to encode the secretable protein, delivering copies of the construct into a liquid suspension culture of tobacco cells, selecting for cells that have acquired the genetic construct, and allowing the desired protein to accumulate in the liquid media in which the plant cells are grown, and isolating the desired protein away from the tobacco cells.

11 Claims, No Drawings

```
                          SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
        (A) LENGTH: 118 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 37..114

(xi) SEQUENCE DESCRIPTION: SEQ ID NO:1:

AAGCTTGGAC AACAACTTTT CTCATTTGTT TCAAAG ATG GGA AAA ATG GCT TCT              54
                                        Met Gly Lys Met Ala Ser
                                         1               5

CTA TTT GCC ACA TTT TTA GTG GTT TTA GTG TCA CTT AGC TTA GCT TCT             102
Leu Phe Ala Thr Phe Leu Val Val Leu Val Ser Leu Ser Leu Ala Ser
             10                  15                  20

GAA AGC TCA GCC ATGG                                                        118
Glu Ser Ser Ala
         25

(2) INFORMATION FOR SEQ ID NO:2:

(i) SEQUENCE CHARACTERISTICS:
        (A) LENGTH: 26 amino acids
        (B) TYPE: amino acid
        (D) TOPOLOGY: linear (ii) MOLECULE TYPE: protein (xi) SEQUENCE DESCRIPTION: SEQ ID NO:2:

Met Gly Lys Met Ala Ser Leu Phe Ala Thr Phe Leu Val Val Leu Val
 1               5                  10                  15

Ser Leu Ser Leu Ala Ser Glu Ser Ser Ala
             20                  25

(2) INFORMATION FOR SEQ ID NO:3:

(i) SEQUENCE CHARACTERISTICS:
```

(A) LENGTH: 103 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 37..99

(xi) SEQUENCE DESCRIPTION: SEQ ID NO:3:

```
AAGCTTGGAC AACAACTTTT CTCATTTGTT TCAAAG ATG GGA AAA ATG GCT TCT        54
                                        Met Gly Lys Met Ala Ser
                                                         30

CTA TTT GCC ACA TTT TTA GTG GTT TTA GTG TCA CTT AGC TTA GCC           99
Leu Phe Ala Thr Phe Leu Val Val Leu Val Ser Leu Ser Leu Ala
         35                  40                  45

ATGG                                                                  103
```

(2) INFORMATION FOR SEQ ID NO:4:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO:4:

```
Met Gly Lys Met Ala Ser Leu Phe Ala Thr Phe Leu Val Val Leu Val
 1               5                  10                  15

Ser Leu Ser Leu Ala
             20
```

(2) INFORMATION FOR SEQ ID NO:5:

(i) SEQUENCE CHARACTERISTICS:
        (A) LENGTH: 166 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:5:

```
AAGCTTGGAC AATCAGCAAT AGTACTACTA CTCCAAGCAA GCATTTTCCT TACAAGTTTG      60

TTTTTCTTGT GATTAATCGA TATGGCTAGC TCAATGTCCC TTAAGCTTGC ATGTGTGGCG     120

GTGTTGTGCA TGGTGGTGGG TGCACCCCTG GCTCAAGGGG CCATGG                   166
```

(2) INFORMATION FOR SEQ ID NO:6:

(i) SEQUENCE CHARACTERISTICS:
        (A) LENGTH: 758 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 3..748

(xi) SEQUENCE DESCRIPTION: SEQ ID NO:6:

```
CC ATG GAT GTG AGC TTT CGT TTA TCA GGT GCT ACA ACC ACA TCC TAT         47
   Met Asp Val Ser Phe Arg Leu Ser Gly Ala Thr Thr Thr Ser Tyr
```

```
            25                  30                  35
GGA GTT TTC ATT AAA AAT CTG AGA GAA GCT CTT CCA TAC GAA AGG AAA       95
Gly Val Phe Ile Lys Asn Leu Arg Glu Ala Leu Pro Tyr Glu Arg Lys
             40                  45                  50

GTG TAC AAT ATA CCG CTA TTA CGT TCA AGT ATT TCA GGT TCA GGA CGC      143
Val Tyr Asn Ile Pro Leu Leu Arg Ser Ser Ile Ser Gly Ser Gly Arg
         55                  60                  65

TAC ACA TTA CTC CAT CTC ACA AAT TAC GCG GAT GAA ACC ATC TCA GTG      191
Tyr Thr Leu Leu His Leu Thr Asn Tyr Ala Asp Glu Thr Ile Ser Val
     70                  75                  80

GCA GTA GAC GTA ACA AAC GTC TAT ATT ATG GGG TAT CTT GCC GGT GAT      239
Ala Val Asp Val Thr Asn Val Tyr Ile Met Gly Tyr Leu Ala Gly Asp
 85                  90                  95                 100

GTG TCC TAT TTT TTC AAC GAG GCT TCA GCA ACA GAA GCT GCA AAA TTC      287
Val Ser Tyr Phe Phe Asn Glu Ala Ser Ala Thr Glu Ala Ala Lys Phe
                105                 110                 115

GTA TTC AAA GAT GCT AAG AAA AAA GTG ACG CTT CCA TAT TCA GGC AAT      335
Val Phe Lys Asp Ala Lys Lys Lys Val Thr Leu Pro Tyr Ser Gly Asn
            120                 125                 130

TAC GAA AGG CTT CAA ACT GCT GCA GGA AAA ATA AGA GAA AAT ATT CCA      383
Tyr Glu Arg Leu Gln Thr Ala Ala Gly Lys Ile Arg Glu Asn Ile Pro
        135                 140                 145

CTT GGA CTC CCA GCT TTG GAC AGT GCC ATT ACC ACT TTG TAT TAC TAC      431
Leu Gly Leu Pro Ala Leu Asp Ser Ala Ile Thr Thr Leu Tyr Tyr Tyr
    150                 155                 160

ACC GCC AGT TCT GCG GCT TCT GCA CTT CTT GTA CTC ATT CAA TCC ACG      479
Thr Ala Ser Ser Ala Ala Ser Ala Leu Leu Val Leu Ile Gln Ser Thr
165                 170                 175                 180

GCT GAA TCT GCA AGG TAT AAA TTT ATT GAA CAA CAA ATT GGA AAG CGT      527
Ala Glu Ser Ala Arg Tyr Lys Phe Ile Glu Gln Gln Ile Gly Lys Arg
                185                 190                 195

GTA GAC AAA ACT TTT TTA CCA AGT TTA GCA ACT ATT AGT TTG GAA AAT      575
Val Asp Lys Thr Phe Leu Pro Ser Leu Ala Thr Ile Ser Leu Glu Asn
            200                 205                 210

AAT TGG TCT GCT CTG TCC AAG CAA ATT CAG ATA GCC AGT ACC AAT AAT      623
Asn Trp Ser Ala Leu Ser Lys Gln Ile Gln Ile Ala Ser Thr Asn Asn
        215                 220                 225

GGA CAA TTT GAG AGT CCT GTT GTG CTT ATA GAT GGT AAC AAC CAA CGA      671
Gly Gln Phe Glu Ser Pro Val Val Leu Ile Asp Gly Asn Asn Gln Arg
    230                 235                 240

GTC TCT ATA ACC AAT GCT AGT GCT CGA GTT GTA ACC TCC AAC ATA GCG      719
Val Ser Ile Thr Asn Ala Ser Ala Arg Val Val Thr Ser Asn Ile Ala
245                 250                 255                 260

TTG CTG CTA AAC AGA AAT AAT ATT GCA    TA GTAACCCGGG               758
Leu Leu Leu Asn Arg Asn Asn Ile Ala
                265

(2) INFORMATION FOR SEQ ID NO:7:

(i) SEQUENCE CHARACTERISTICS:
        (A) LENGTH: 248 amino acids
        (B) TYPE: amino acid
        (D) TOPOLOGY: linear (ii) MOLECULE TYPE: protein (xi) SEQUENCE DESCRIPTION: SEQ ID NO:7:

Met Asp Val Ser Phe Arg Leu Ser Gly Ala Thr Thr Thr Ser Tyr Gly
  1               5                  10                  15

Val Phe Ile Lys Asn Leu Arg Glu Ala Leu Pro Tyr Glu Arg Lys Val
             20                  25                  30
```

```
Tyr Asn Ile Pro Leu Leu Arg Ser Ser Ile Ser Gly Ser Gly Arg Tyr
        35                  40                  45

Thr Leu Leu His Leu Thr Asn Tyr Ala Asp Glu Thr Ile Ser Val Ala
 50                  55                  60

Val Asp Val Thr Asn Val Tyr Ile Met Gly Tyr Leu Ala Gly Asp Val
 65                  70                  75                  80

Ser Tyr Phe Phe Asn Glu Ala Ser Ala Thr Glu Ala Ala Lys Phe Val
                 85                  90                  95

Phe Lys Asp Ala Lys Lys Val Thr Leu Pro Tyr Ser Gly Asn Tyr
            100                 105                 110

Glu Arg Leu Gln Thr Ala Ala Gly Lys Ile Arg Glu Asn Ile Pro Leu
            115                 120                 125

Gly Leu Pro Ala Leu Asp Ser Ala Ile Thr Thr Leu Tyr Tyr Tyr Thr
130                 135                 140

Ala Ser Ser Ala Ala Ser Ala Leu Leu Val Leu Ile Gln Ser Thr Ala
145                 150                 155                 160

Glu Ser Ala Arg Tyr Lys Phe Ile Glu Gln Gln Ile Gly Lys Arg Val
                165                 170                 175

Asp Lys Thr Phe Leu Pro Ser Leu Ala Thr Ile Ser Leu Glu Asn Asn
            180                 185                 190

Trp Ser Ala Leu Ser Lys Gln Ile Gln Ile Ala Ser Thr Asn Asn Gly
            195                 200                 205

Gln Phe Glu Ser Pro Val Val Leu Ile Asp Gly Asn Asn Gln Arg Val
        210                 215                 220

Ser Ile Thr Asn Ala Ser Ala Arg Val Val Thr Ser Asn Ile Ala Leu
225                 230                 235                 240

Leu Leu Asn Arg Asn Asn Ile Ala
                245

(2) INFORMATION FOR SEQ ID NO:8:

(i) SEQUENCE CHARACTERISTICS:
        (A) LENGTH: 759 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..759

(xi) SEQUENCE DESCRIPTION: SEQ ID NO:8:

ATG GCC GCA TCT AGA CAA ATT GTT CTC TCC CAG TCT CCA GCA ATC CTG      48
Met Ala Ala Ser Arg Gln Ile Val Leu Ser Gln Ser Pro Ala Ile Leu
250                 255                 260

TCT GCA TCT CCA GGG GAG AAG GTC ACA TTG ACT TGC AGG GCC AGC TCA      96
Ser Ala Ser Pro Gly Glu Lys Val Thr Leu Thr Cys Arg Ala Ser Ser
265                 270                 275                 280

AGT GTA AGT TTC ATG AAC TGG TAC CAG CAG TGT CCA GGA TCC TCC CCC     144
Ser Val Ser Phe Met Asn Trp Tyr Gln Gln Cys Pro Gly Ser Ser Pro
                285                 290                 295

AAA CCC TGG ATT TAT GCC ACA TCC AAT TTG GCT TCT GGA GTC CCT GGT     192
Lys Pro Trp Ile Tyr Ala Thr Ser Asn Leu Ala Ser Gly Val Pro Gly
            300                 305                 310

CGC TTC AGT GGC AGT GGG TCT GGG ACC TCT TAC TCT CTC GCA ATC AGC     240
Arg Phe Ser Gly Ser Gly Ser Gly Thr Ser Tyr Ser Leu Ala Ile Ser
        315                 320                 325
```

```
AGA GTG GAG GCT GAA GAT GCT GCC ACT TAT TAC TGC CAG CAG TGG AAT        288
Arg Val Glu Ala Glu Asp Ala Ala Thr Tyr Tyr Cys Gln Gln Trp Asn
        330                 335                 340

AGT AAC CCA CTC ACG TTC GGT GCT GGG ACC AAG CTG GAG CTG AAA GAG        336
Ser Asn Pro Leu Thr Phe Gly Ala Gly Thr Lys Leu Glu Leu Lys Glu
345                 350                 355                 360

CTC TCT GGT GGC GGT GGC TCG GGC GGT GGT GGG TCG GGT GGC GGC GGA        384
Leu Ser Gly Gly Gly Gly Ser Gly Gly Gly Gly Ser Gly Gly Gly Gly
                365                 370                 375

TCT CTG CAG ATC CAG TTG GTG CAG TCT GGA CCT GAG CTG AAG AAG CCT        432
Ser Leu Gln Ile Gln Leu Val Gln Ser Gly Pro Glu Leu Lys Lys Pro
            380                 385                 390

GGA GAG ACA GTC AAG ATC TCC TGC AAG GCT TCT GGG TAT ACC TTC ACA        480
Gly Glu Thr Val Lys Ile Ser Cys Lys Ala Ser Gly Tyr Thr Phe Thr
        395                 400                 405

AAC TAT GGA ATG AAC TGG GTG AAG CAG GCT CCA GGA AAG GGT TTA AAG        528
Asn Tyr Gly Met Asn Trp Val Lys Gln Ala Pro Gly Lys Gly Leu Lys
410                 415                 420

TGG ATG GGC TGG ATA AAC ACC TAC ACT GGA CAG CCA ACA TAT GCT GAT        576
Trp Met Gly Trp Ile Asn Thr Tyr Thr Gly Gln Pro Thr Tyr Ala Asp
425                 430                 435                 440

GAC TTC AAG GGA CGG TTT GCC TTC TCT TTG GAA ACC TCT GCC TAC ACT        624
Asp Phe Lys Gly Arg Phe Ala Phe Ser Leu Glu Thr Ser Ala Tyr Thr
                445                 450                 455

GCC TAT TTG CAG ATC AAC AAC CTC AAA AAT GAG GAC ATG GCT ACA TAT        672
Ala Tyr Leu Gln Ile Asn Asn Leu Lys Asn Glu Asp Met Ala Thr Tyr
            460                 465                 470

TTC TGT GCA AGA TTT AGC TAT GGT AAC TCA CGT TAC GCT GAC TAC TGG        720
Phe Cys Ala Arg Phe Ser Tyr Gly Asn Ser Arg Tyr Ala Asp Tyr Trp
        475                 480                 485

GGC CAA GGC ACC ACT CTC ACA GTC TCA CCC GGG TAG                        759
Gly Gln Gly Thr Thr Leu Thr Val Ser Ser Pro Gly  *
490                 495                 500

(2) INFORMATION FOR SEQ ID NO:9:

(i) SEQUENCE CHARACTERISTICS:
            (A) LENGTH:  252 amino acids
            (B) TYPE: amino acid
            (D) TOPOLOGY: linear (ii) MOLECULE TYPE: protein (xi) SEQUENCE DESCRIPTION: SEQ ID NO:9:

Met Ala Ala Ser Arg Gln Ile Val Leu Ser Gln Ser Pro Ala Ile Leu
 1               5                  10                  15

Ser Ala Ser Pro Gly Glu Lys Val Thr Leu Thr Cys Arg Ala Ser Ser
                20                  25                  30

Ser Val Ser Phe Met Asn Trp Tyr Gln Gln Cys Pro Gly Ser Ser Pro
            35                  40                  45

Lys Pro Trp Ile Tyr Ala Thr Ser Asn Leu Ala Ser Gly Val Pro Gly
        50                  55                  60

Arg Phe Ser Gly Ser Gly Ser Gly Thr Ser Tyr Ser Leu Ala Ile Ser
65                  70                  75                  80

Arg Val Glu Ala Glu Asp Ala Ala Thr Tyr Tyr Cys Gln Gln Trp Asn
                85                  90                  95

Ser Asn Pro Leu Thr Phe Gly Ala Gly Thr Lys Leu Glu Leu Lys Glu
            100                 105                 110

Leu Ser Gly Gly Gly Gly Ser Gly Gly Gly Gly Ser Gly Gly Gly Gly
```

```
            115                 120                 125
Ser Leu Gln Ile Gln Leu Val Gln Ser Gly Pro Glu Leu Lys Lys Pro
    130                 135                 140

Gly Glu Thr Val Lys Ile Ser Cys Lys Ala Ser Gly Tyr Thr Phe Thr
145                 150                 155                 160

Asn Tyr Gly Met Asn Trp Val Lys Gln Ala Pro Gly Lys Gly Leu Lys
                165                 170                 175

Trp Met Gly Trp Ile Asn Thr Tyr Thr Gly Gln Pro Thr Tyr Ala Asp
                180                 185                 190

Asp Phe Lys Gly Arg Phe Ala Phe Ser Leu Glu Thr Ser Ala Tyr Thr
            195                 200                 205

Ala Tyr Leu Gln Ile Asn Asn Leu Lys Asn Glu Asp Met Ala Thr Tyr
    210                 215                 220

Phe Cys Ala Arg Phe Ser Tyr Gly Asn Ser Arg Tyr Ala Asp Tyr Trp
225                 230                 235                 240

Gly Gln Gly Thr Thr Leu Thr Val Ser Ser Pro Gly
                245                 250

(2) INFORMATION FOR SEQ ID NO:10:

(i) SEQUENCE CHARACTERISTICS:
        (A) LENGTH: 720 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..719

(ix) FEATURE:
        (A) NAME/KEY: CDS
        (B) LOCATION: 1..720

(xi) SEQUENCE DESCRIPTION: SEQ ID NO:10:

ATG GCC CAG GTC CAG CTT CAG CAG TCT GGG GCT GAA CTG GCA AAA CCT      48
Met Ala Gln Val Gln Leu Gln Gln Ser Gly Ala Glu Leu Ala Lys Pro
    255                 260                 265

GGG GCC TCA GTG AAG ATG TCC TGC AAG GCT TCT GGC TAC ACC TTT ACT      96
Gly Ala Ser Val Lys Met Ser Cys Lys Ala Ser Gly Tyr Thr Phe Thr
270                 275                 280                 285

AGC TAC AGG ATG CAC TGG GTA AAA CAG AGG CCT GGA CAG GGT CTG GAA     144
Ser Tyr Arg Met His Trp Val Lys Gln Arg Pro Gly Gln Gly Leu Glu
                290                 295                 300

TGG ATT GGA TAT ATT AAT CCT AGC ACT GGG TAT ACT GAA TAC AAT CAG     192
Trp Ile Gly Tyr Ile Asn Pro Ser Thr Gly Tyr Thr Glu Tyr Asn Gln
            305                 310                 315

AAG TTC AAG GAC AAG GCC ACA TTG ACT GCA GAC AAA TCC TCC AGC ACA     240
Lys Phe Lys Asp Lys Ala Thr Leu Thr Ala Asp Lys Ser Ser Ser Thr
    320                 325                 330

GCC TAC ATG CAA CTG AGC AGC CTG ACA TTT GAG GAC TCT GCA GTC TAT     288
Ala Tyr Met Gln Leu Ser Ser Leu Thr Phe Glu Asp Ser Ala Val Tyr
335                 340                 345

TAC TGT GCA AGA GGG GGG GGG GTC TTT GAC TAC TGG GGC CAA GGA ACC     336
Tyr Cys Ala Arg Gly Gly Gly Val Phe Asp Tyr Trp Gly Gln Gly Thr
350                 355                 360                 365

ACT CTC ACA GTC TCC TCC GGA GGC GGT GGC TCG GGC GGT GGC GGC TCG     384
Thr Leu Thr Val Ser Ser Gly Gly Gly Gly Ser Gly Gly Gly Gly Ser
                370                 375                 380
```

```
GGT GGC GGC GGC TCT CAA ATT GTT CTC ACC CAG TCT CCA GCA ATC ATG    432
Gly Gly Gly Gly Ser Gln Ile Val Leu Thr Gln Ser Pro Ala Ile Met
            385                 390                 395

TCT GCA TCT CCA GGG GAG AAG GTC ACC ATA ACC TGC AGT GCC AGC TCA    480
Ser Ala Ser Pro Gly Glu Lys Val Thr Ile Thr Cys Ser Ala Ser Ser
                400                 405                 410

AGT ATA AGT TAC ATG CAC TGG TTC CAG CAG AAG CCA GGC ACT TCT CCC    528
Ser Ile Ser Tyr Met His Trp Phe Gln Gln Lys Pro Gly Thr Ser Pro
        415                 420                 425

AAA CTC TGG ATT TAT ACC ACA TCC AAC CTG GCT TCT GGA GTC CCT GCT    576
Lys Leu Trp Ile Tyr Thr Thr Ser Asn Leu Ala Ser Gly Val Pro Ala
430                 435                 440                 445

CGC TTC AGT GGC AGT GGA TCT GGG ACC TCT TAC TCT CTC ACA ATC AGC    624
Arg Phe Ser Gly Ser Gly Ser Gly Thr Ser Tyr Ser Leu Thr Ile Ser
                450                 455                 460

CGA ATG GAG GCT GAA GAT GCT GCC ACT TAT TAC TGC CAT CAA AGG AGT    672
Arg Met Glu Ala Glu Asp Ala Ala Thr Tyr Tyr Cys His Gln Arg Ser
            465                 470                 475

ACT TAC CCA CTC ACG TTC GGT TCT GGG ACC AAG CTG GAG CTC AAG TAG    720
Thr Tyr Pro Leu Thr Phe Gly Ser Gly Thr Lys Leu Glu Leu Lys  *
        480                 485                 490

(2) INFORMATION FOR SEQ ID NO:11:

(i) SEQUENCE CHARACTERISTICS:
        (A) LENGTH:  239 amino acids
        (B) TYPE: amino acid
        (D) TOPOLOGY: linear (ii) MOLECULE TYPE: protein (xi) SEQUENCE DESCRIPTION: SEQ ID NO:11:

Met Ala Gln Val Gln Leu Gln Gln Ser Gly Ala Glu Leu Ala Lys Pro
 1               5                  10                  15

Gly Ala Ser Val Lys Met Ser Cys Lys Ala Ser Gly Tyr Thr Phe Thr
                20                  25                  30

Ser Tyr Arg Met His Trp Val Lys Gln Arg Pro Gly Gln Gly Leu Glu
            35                  40                  45

Trp Ile Gly Tyr Ile Asn Pro Ser Thr Gly Tyr Thr Glu Tyr Asn Gln
    50                  55                  60

Lys Phe Lys Asp Lys Ala Thr Leu Thr Ala Asp Lys Ser Ser Ser Thr
65                  70                  75                  80

Ala Tyr Met Gln Leu Ser Ser Leu Thr Phe Glu Asp Ser Ala Val Tyr
                85                  90                  95

Tyr Cys Ala Arg Gly Gly Gly Val Phe Asp Tyr Trp Gly Gln Gly Thr
            100                 105                 110

Thr Leu Thr Val Ser Ser Gly Gly Gly Gly Ser Gly Gly Gly Gly Ser
    115                 120                 125

Gly Gly Gly Gly Ser Gln Ile Val Leu Thr Gln Ser Pro Ala Ile Met
130                 135                 140

Ser Ala Ser Pro Gly Glu Lys Val Thr Ile Thr Cys Ser Ala Ser Ser
145                 150                 155                 160

Ser Ile Ser Tyr Met His Trp Phe Gln Gln Lys Pro Gly Thr Ser Pro
                165                 170                 175

Lys Leu Trp Ile Tyr Thr Thr Ser Asn Leu Ala Ser Gly Val Pro Ala
            180                 185                 190

Arg Phe Ser Gly Ser Gly Ser Gly Thr Ser Tyr Ser Leu Thr Ile Ser
        195                 200                 205
```

```
Arg Met Glu Ala Glu Asp Ala Ala Thr Tyr Tyr Cys His Gln Arg Ser
    210                 215                 220
Thr Tyr Pro Leu Thr Phe Gly Ser Gly Thr Lys Leu Glu Leu Lys
225                 230                 235                 240
```

(2) INFORMATION FOR SEQ ID NO:12:

(i) SEQUENCE CHARACTERISTICS:
        (A) LENGTH: 734 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 3..728

(xi) SEQUENCE DESCRIPTION: SEQ ID NO:12:

```
CC ATG GAT GCT GTG ATG ACC CAA AAT CCA CTC TCC CTG CCT GTC AGT          47
   Met Asp Ala Val Met Thr Gln Asn Pro Leu Ser Leu Pro Val Ser
                       245                 250                 255

CTT GGA GAT GAA GCC TCC ATC TCT TGC AGG TCA AGT CAG AGT CTT GAA         95
Leu Gly Asp Glu Ala Ser Ile Ser Cys Arg Ser Ser Gln Ser Leu Glu
                260                 265                 270

AAC AGT AAT GGA AAC ACC TTT TTG AAC TGG TTC TTC CAG AAA CCA GGC        143
Asn Ser Asn Gly Asn Thr Phe Leu Asn Trp Phe Phe Gln Lys Pro Gly
            275                 280                 285

CAG TCT CCA CAG CTC CTG ATC TAC AGG GTT TCC AAC CGA TTT TCT GGG        191
Gln Ser Pro Gln Leu Leu Ile Tyr Arg Val Ser Asn Arg Phe Ser Gly
        290                 295                 300

GTC CCA GAC AGG TTC AGC GGT AGT GGA TCA GGG ACA GAT TTC ACA CTG        239
Val Pro Asp Arg Phe Ser Gly Ser Gly Ser Gly Thr Asp Phe Thr Leu
    305                 310                 315

AAG ATC AGC AGA GTG GAG GCT GAG GAT TTG GGA GTT TAT TTC TGC CTC        287
Lys Ile Ser Arg Val Glu Ala Glu Asp Leu Gly Val Tyr Phe Cys Leu
320                 325                 330                 335

CAA GTT ACA CAT GTC CCG TAC ACG TTC GGA GGG GGG ACC ACG CTG GAA        335
Gln Val Thr His Val Pro Tyr Thr Phe Gly Gly Gly Thr Thr Leu Glu
                340                 345                 350

ATA AAA CGG GGT GGC GGT GGC TCG GGC GGA GGT GGG TCG GGT GGC GGC        383
Ile Lys Arg Gly Gly Gly Gly Ser Gly Gly Gly Gly Ser Gly Gly Gly
            355                 360                 365

GGA TCT GAT ATA CAG CTT CAG CAG TCA GGA CCT GGC CTC GTG AAA CCT        431
Gly Ser Asp Ile Gln Leu Gln Gln Ser Gly Pro Gly Leu Val Lys Pro
        370                 375                 380

TCT CAG TCT CTG TCT CTC ACC TGC TCT GTC ACT GGC TAC TCC ATC ACC        479
Ser Gln Ser Leu Ser Leu Thr Cys Ser Val Thr Gly Tyr Ser Ile Thr
    385                 390                 395

ACT AAT TAT AAC TGG AAC TGG ATC CGG CAG TTT CCA GGA AAC AAA CTG        527
Thr Asn Tyr Asn Trp Asn Trp Ile Arg Gln Phe Pro Gly Asn Lys Leu
400                 405                 410                 415

GAA TGG ATG GGC TAC ATA AGG TAC GAC GGT ACT AGT GAG TAC ACC CCA        575
Glu Trp Met Gly Tyr Ile Arg Tyr Asp Gly Thr Ser Glu Tyr Thr Pro
                420                 425                 430

TCT CTC AAA AAT CGA GTC TCC ATC ACT CGT GAC ACA TCT ATG AAT CAG        623
Ser Leu Lys Asn Arg Val Ser Ile Thr Arg Asp Thr Ser Met Asn Gln
            435                 440                 445

TTT TTC CTG AGA TTG ACT TCT GTG ACT CCT GAG GAC ACA GCG ACG TAT        671
Phe Phe Leu Arg Leu Thr Ser Val Thr Pro Glu Asp Thr Ala Thr Tyr
        450                 455                 460
```

```
TAT TGT GCA AGG TTG GAC TAT TGG GGT CAA GGA ACC TCA GTC ACC GTC                         719
Tyr Cys Ala Arg Leu Asp Tyr Trp Gly Gln Gly Thr Ser Val Thr Val
    465                 470                 475

TCC TCA TAG CCCGGG                                                                      734
Ser Ser *
480
```

(2) INFORMATION FOR SEQ ID NO:13:

(i) SEQUENCE CHARACTERISTICS:
        (A) LENGTH: 241 amino acids
        (B) TYPE: amino acid
        (D) TOPOLOGY: linear (ii) MOLECULE TYPE: protein (xi) SEQUENCE DESCRIPTION: SEQ ID NO:13:

```
Met Asp Ala Val Met Thr Gln Asn Pro Leu Ser Leu Pro Val Ser Leu
1               5                   10                  15

Gly Asp Glu Ala Ser Ile Ser Cys Arg Ser Ser Gln Ser Leu Glu Asn
                20                  25                  30

Ser Asn Gly Asn Thr Phe Leu Asn Trp Phe Gln Lys Pro Gly Gln
        35                  40                  45

Ser Pro Gln Leu Leu Ile Tyr Arg Val Ser Asn Arg Phe Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Leu Gly Val Tyr Phe Cys Leu Gln
                85                  90                  95

Val Thr His Val Pro Tyr Thr Phe Gly Gly Gly Thr Thr Leu Glu Ile
                100                 105                 110

Lys Arg Gly Gly Gly Gly Ser Gly Gly Gly Ser Gly Gly Gly Gly
            115                 120                 125

Ser Asp Ile Gln Leu Gln Gln Ser Gly Pro Gly Leu Val Lys Pro Ser
    130                 135                 140

Gln Ser Leu Ser Leu Thr Cys Ser Val Thr Gly Tyr Ser Ile Thr Thr
145                 150                 155                 160

Asn Tyr Asn Trp Asn Trp Ile Arg Gln Phe Pro Gly Asn Lys Leu Glu
                165                 170                 175

Trp Met Gly Tyr Ile Arg Tyr Asp Gly Thr Ser Glu Tyr Thr Pro Ser
            180                 185                 190

Leu Lys Asn Arg Val Ser Ile Thr Arg Asp Thr Ser Met Asn Gln Phe
        195                 200                 205

Phe Leu Arg Leu Thr Ser Val Thr Pro Glu Asp Thr Ala Thr Tyr Tyr
    210                 215                 220

Cys Ala Arg Leu Asp Tyr Trp Gly Gln Gly Thr Ser Val Thr Val Ser
225                 230                 235                 240

Ser *
```

(2) INFORMATION FOR SEQ ID NO:14:

(i) SEQUENCE CHARACTERISTICS:
        (A) LENGTH: 1499 base pairs
        (B) TYPE: nucleic acid
        (C) STRANDEDNESS: double
        (D) TOPOLOGY: linear (ii) MOLECULE TYPE: cDNA (ix) FEATURE:

(A) NAME/KEY: CDS
(B) LOCATION: 3..1493

(xi) SEQUENCE DESCRIPTION: SEQ ID NO:14:

| | | |
|---|---|---|
| CC ATG GAT GTG AGC TTT CGT TTA TCA GGT GCT ACA ACC ACA TCC TAT<br>   Met Asp Val Ser Phe Arg Leu Ser Gly Ala Thr Thr Thr Ser Tyr<br>      245                  250                  255 | 47 |
| GGA GTT TTC ATT AAA AAT CTG AGA GAA GCT CTT CCA TAC GAA AGG AAA<br>Gly Val Phe Ile Lys Asn Leu Arg Glu Ala Leu Pro Tyr Glu Arg Lys<br>        260                 265              270 | 95 |
| GTG TAC AAT ATA CCG CTA TTA CGT TCA AGT ATT TCA GGT TCA GGA CGC<br>Val Tyr Asn Ile Pro Leu Leu Arg Ser Ser Ile Ser Gly Ser Gly Arg<br> 275                 280               285 | 143 |
| TAC ACA TTA CTC CAT CTC ACA AAT TAC GCG GAT GAA ACC ATC TCA GTG<br>Tyr Thr Leu Leu His Leu Thr Asn Tyr Ala Asp Glu Thr Ile Ser Val<br>290               295               300              305 | 191 |
| GCA GTA GAC GTA ACA AAC GTC TAT ATT ATG GGG TAT CTT GCC GGT GAT<br>Ala Val Asp Val Thr Asn Val Tyr Ile Met Gly Tyr Leu Ala Gly Asp<br>             310              315              320 | 239 |
| GTG TCC TAT TTT TTC AAC GAG GCT TCA GCA ACA GAA GCT GCA AAA TTC<br>Val Ser Tyr Phe Phe Asn Glu Ala Ser Ala Thr Glu Ala Ala Lys Phe<br>       325                330              335 | 287 |
| GTA TTC AAA GAT GCT AAG AAA AAA GTG ACG CTT CCA TAT TCA GGC AAT<br>Val Phe Lys Asp Ala Lys Lys Lys Val Thr Leu Pro Tyr Ser Gly Asn<br>   340                345              350 | 335 |
| TAC GAA AGG CTT CAA ACT GCT GCA GGA AAA ATA AGA GAA AAT ATT CCA<br>Tyr Glu Arg Leu Gln Thr Ala Ala Gly Lys Ile Arg Glu Asn Ile Pro<br>355               360               365 | 383 |
| CTT GGA CTC CCA GCT TTG GAC AGT GCC ATT ACC ACT TTG TAT TAC TAC<br>Leu Gly Leu Pro Ala Leu Asp Ser Ala Ile Thr Thr Leu Tyr Tyr Tyr<br>370               375              380             385 | 431 |
| ACC GCC AGT TCT GCG GCT TCT GCA CTT CTT GTA CTC ATT CAA TCC ACG<br>Thr Ala Ser Ser Ala Ala Ser Ala Leu Leu Val Leu Ile Gln Ser Thr<br>             390              395              400 | 479 |
| GCT GAA TCT GCA AGG TAT AAA TTT ATT GAA CAA CAA ATT GGA AAG CGT<br>Ala Glu Ser Ala Arg Tyr Lys Phe Ile Glu Gln Gln Ile Gly Lys Arg<br>       405                410              415 | 527 |
| GTA GAC AAA ACT TTT TTA CCA AGT TTA GCA ACT ATT AGT TTG GAA AAT<br>Val Asp Lys Thr Phe Leu Pro Ser Leu Ala Thr Ile Ser Leu Glu Asn<br>   420                425              430 | 575 |
| AAT TGG TCT GCT CTG TCC AAG CAA ATT CAG ATA GCC AGT ACC AAT AAT<br>Asn Trp Ser Ala Leu Ser Lys Gln Ile Gln Ile Ala Ser Thr Asn Asn<br>435               440               445 | 623 |
| GGA CAA TTT GAG AGT CCT GTT GTG CTT ATA GAT GGT AAC AAC CAA CGA<br>Gly Gln Phe Glu Ser Pro Val Val Leu Ile Asp Gly Asn Asn Gln Arg<br>450               455              460             465 | 671 |
| GTC TCT ATA ACC AAT GCT AGT GCT CGA GTT GTA ACC TCC AAC ATA GCG<br>Val Ser Ile Thr Asn Ala Ser Ala Arg Val Val Thr Ser Asn Ile Ala<br>             470              475              480 | 719 |
| TTG CTG CTA AAC AGA AAT AAT ATT GCA CGC ATG CAT GGT ACC AAG GCC<br>Leu Leu Leu Asn Arg Asn Asn Ile Ala Arg Met His Gly Thr Lys Ala<br>       485                490              495 | 767 |
| ATG GAT GCT GTG ATG ACC CAA AAT CCA CTC TCC CTG CCT GTC AGT CTT<br>Met Asp Ala Val Met Thr Gln Asn Pro Leu Ser Leu Pro Val Ser Leu<br>   500                505              510 | 815 |
| GGA GAT GAA GCC TCC ATC TCT TGC AGG TCA AGT CAG AGT CTT GAA AAC<br>Gly Asp Glu Ala Ser Ile Ser Cys Arg Ser Ser Gln Ser Leu Glu Asn<br>515               520              525 | 863 |
| AGT AAT GGA AAC ACC TTT TTG AAC TGG TTC TTC CAG AAA CCA GGC CAG<br>Ser Asn Gly Asn Thr Phe Leu Asn Trp Phe Phe Gln Lys Pro Gly Gln | 911 |

```
530                    535                     540                     545
TCT CCA CAG CTC CTG ATC TAC AGG GTT TCC AAC CGA TTT TCT GGG GTC              959
Ser Pro Gln Leu Leu Ile Tyr Arg Val Ser Asn Arg Phe Ser Gly Val
            550                     555                     560

CCA GAC AGG TTC AGC GGT AGT GGA TCA GGG ACA GAT TTC ACA CTG AAG             1007
Pro Asp Arg Phe Ser Gly Ser Gly Ser Gly Thr Asp Phe Thr Leu Lys
            565                     570                     575

ATC AGC AGA GTG GAG GCT GAG GAT TTG GGA GTT TAT TTC TGC CTC CAA             1055
Ile Ser Arg Val Glu Ala Glu Asp Leu Gly Val Tyr Phe Cys Leu Gln
            580                     585                     590

GTT ACA CAT GTC CCG TAC ACG TTC GGA GGG GGG ACC ACG CTG GAA ATA             1103
Val Thr His Val Pro Tyr Thr Phe Gly Gly Gly Thr Thr Leu Glu Ile
            595                     600                     605

AAA CGG GGT GGC GGT GGC TCG GGC GGA GGT GGG TCG GGT GGC GGC GGA             1151
Lys Arg Gly Gly Gly Gly Ser Gly Gly Gly Gly Ser Gly Gly Gly Gly
610                     615                     620                     625

TCT GAT ATA CAG CTT CAG CAG TCA GGA CCT GGC CTC GTG AAA CCT TCT             1199
Ser Asp Ile Gln Leu Gln Gln Ser Gly Pro Gly Leu Val Lys Pro Ser
            630                     635                     640

CAG TCT CTG TCT CTC ACC TGC TCT GTC ACT GGC TAC TCC ATC ACC ACT             1247
Gln Ser Leu Ser Leu Thr Cys Ser Val Thr Gly Tyr Ser Ile Thr Thr
            645                     650                     655

AAT TAT AAC TGG AAC TGG ATC CGG CAG TTT CCA GGA AAC AAA CTG GAA             1295
Asn Tyr Asn Trp Asn Trp Ile Arg Gln Phe Pro Gly Asn Lys Leu Glu
            660                     665                     670

TGG ATG GGC TAC ATA AGG TAC GAC GGT ACT AGT GAG TAC ACC CCA TCT             1343
Trp Met Gly Tyr Ile Arg Tyr Asp Gly Thr Ser Glu Tyr Thr Pro Ser
            675                     680                     685

CTC AAA AAT CGA GTC TCC ATC ACT CGT GAC ACA TCT ATG AAT CAG TTT             1391
Leu Lys Asn Arg Val Ser Ile Thr Arg Asp Thr Ser Met Asn Gln Phe
690                     695                     700                     705

TTC CTG AGA TTG ACT TCT GTG ACT CCT GAG GAC ACA GCG ACG TAT TAT             1439
Phe Leu Arg Leu Thr Ser Val Thr Pro Glu Asp Thr Ala Thr Tyr Tyr
            710                     715                     720

TGT GCA AGG TTG GAC TAT TGG GGT CAA GGA ACC TCA GTC ACC GTC TCC             1487
Cys Ala Arg Leu Asp Tyr Trp Gly Gln Gly Thr Ser Val Thr Val Ser
            725                     730                     735

TCA TAG CCCGGG                                                              1499
Ser *
```

(2) INFORMATION FOR SEQ ID NO:15:

(i) SEQUENCE CHARACTERISTICS:
        (A) LENGTH: 496 amino acids
        (B) TYPE: amino acid
        (D) TOPOLOGY: linear (ii) MOLECULE TYPE: protein (xi) SEQUENCE DESCRIPTION: SEQ ID NO:15:

```
Met Asp Val Ser Phe Arg Leu Ser Gly Ala Thr Thr Thr Ser Tyr Gly
1               5                   10                  15

Val Phe Ile Lys Asn Leu Arg Glu Ala Leu Pro Tyr Glu Arg Lys Val
            20                  25                  30

Tyr Asn Ile Pro Leu Leu Arg Ser Ser Ile Ser Gly Ser Gly Arg Tyr
            35                  40                  45

Thr Leu Leu His Leu Thr Asn Tyr Ala Asp Glu Thr Ile Ser Val Ala
            50                  55                  60

Val Asp Val Thr Asn Val Tyr Ile Met Gly Tyr Leu Ala Gly Asp Val
65                  70                  75                  80
```

```
Ser Tyr Phe Phe Asn Glu Ala Ser Ala Thr Glu Ala Lys Phe Val
                85                  90                  95

Phe Lys Asp Ala Lys Lys Val Thr Leu Pro Tyr Ser Gly Asn Tyr
            100                 105                 110

Glu Arg Leu Gln Thr Ala Ala Gly Lys Ile Arg Glu Asn Ile Pro Leu
        115                 120                 125

Gly Leu Pro Ala Leu Asp Ser Ala Ile Thr Thr Leu Tyr Tyr Tyr Thr
    130                 135                 140

Ala Ser Ser Ala Ala Ser Ala Leu Leu Val Leu Ile Gln Ser Thr Ala
145                 150                 155                 160

Glu Ser Ala Arg Tyr Lys Phe Ile Glu Gln Gln Ile Gly Lys Arg Val
                165                 170                 175

Asp Lys Thr Phe Leu Pro Ser Leu Ala Thr Ile Ser Leu Glu Asn Asn
            180                 185                 190

Trp Ser Ala Leu Ser Lys Gln Ile Gln Ile Ala Ser Thr Asn Asn Gly
        195                 200                 205

Gln Phe Glu Ser Pro Val Val Leu Ile Asp Gly Asn Asn Gln Arg Val
    210                 215                 220

Ser Ile Thr Asn Ala Ser Ala Arg Val Val Thr Ser Asn Ile Ala Leu
225                 230                 235                 240

Leu Leu Asn Arg Asn Asn Ile Ala Arg Met His Gly Thr Lys Ala Met
                245                 250                 255

Asp Ala Val Met Thr Gln Asn Pro Leu Ser Leu Pro Val Ser Leu Gly
            260                 265                 270

Asp Glu Ala Ser Ile Ser Cys Arg Ser Ser Gln Ser Leu Glu Asn Ser
        275                 280                 285

Asn Gly Asn Thr Phe Leu Asn Trp Phe Phe Gln Lys Pro Gly Gln Ser
    290                 295                 300

Pro Gln Leu Leu Ile Tyr Arg Val Ser Asn Arg Phe Ser Gly Val Pro
305                 310                 315                 320

Asp Arg Phe Ser Gly Ser Gly Ser Gly Thr Asp Phe Thr Leu Lys Ile
                325                 330                 335

Ser Arg Val Glu Ala Glu Asp Leu Gly Val Tyr Phe Cys Leu Gln Val
            340                 345                 350

Thr His Val Pro Tyr Thr Phe Gly Gly Gly Thr Thr Leu Glu Ile Lys
        355                 360                 365

Arg Gly Gly Gly Gly Ser Gly Gly Gly Ser Gly Gly Gly Gly Ser
    370                 375                 380

Asp Ile Gln Leu Gln Gln Ser Gly Pro Gly Leu Val Lys Pro Ser Gln
385                 390                 395                 400

Ser Leu Ser Leu Thr Cys Ser Val Thr Gly Tyr Ser Ile Thr Thr Asn
                405                 410                 415

Tyr Asn Trp Asn Trp Ile Arg Gln Phe Pro Gly Asn Lys Leu Glu Trp
            420                 425                 430

Met Gly Tyr Ile Arg Tyr Asp Gly Thr Ser Glu Tyr Thr Pro Ser Leu
        435                 440                 445

Lys Asn Arg Val Ser Ile Thr Arg Asp Thr Ser Met Asn Gln Phe Phe
450                 455                 460

Leu Arg Leu Thr Ser Val Thr Pro Glu Asp Thr Ala Thr Tyr Tyr Cys
465                 470                 475                 480

Ala Arg Leu Asp Tyr Trp Gly Gln Gly Thr Ser Val Thr Val Ser Ser
                485                 490                 495
```

METHOD FOR PRODUCING ANTIBODIES AND PROTEIN TOXINS IN PLANT CELLS

CROSS-REFERENCE TO RELATED APPLICATIONS

This patent application is a Continuation-in-part of U.S. patent application Ser. No. 08/279,772, filed Jul. 25, 1994.

STATEMENT REGARDING FEDERALLY SPONSORED RESEARCH OR DEVELOPMENT

Not applicable.

BACKGROUND OF THE INVENTION

Within the medical sciences, there is growing interest in the potential utility of purified mammalian antibodies in the diagnosis and treatment of disease. Utilization of the exquisite specificity of particular antibodies for their antigenic determinants has revolutionized the ways in which diseases are described, diagnosed and treated.

For example, tagged antibodies directed against tumor cell surface antigens provide a highly sensitive and specific means for detecting and classifying various cancers. Antibodies also have tremendous potential in the treatment of cancers. One therapeutic application using antibodies involves the administration of purified tumor-specific antibodies that are chemically coupled to cytotoxic agents. A class of cytotoxins that holds particular promise in the treatment of cancers consists of protein toxins from plants. However, progress in the treatment of cancers using chemically coupled antibodies and cytotoxins has been impeded by the lack of a cost effective means for producing these molecules in a pharmaceutically acceptable grade and in commercially acceptable quantities.

Despite recent advances in in vitro antibody synthesis, the production and purification of antibodies remains a costly and time-consuming endeavor. Existing commercial methods require large colonies of laboratory animals or large scale cell culture facilities, each of which is expensive to establish and maintain. In addition, purification of antibodies derived from animals or animal cell culture is a laborious process, because many contaminating biomolecules must be removed from the preparation without destroying the conformational integrity and biological activity of the antibodies.

Obtaining large quantities of purified toxins having potential utility as chemotherapeutics has also proven problematic. The potential for using cloned toxin-encoding DNA sequences to obtain commercial quantities of toxin has not been fully exploited. This is due primarily to difficulties associated with finding a suitable expression system. Generally, toxins expressed in transgenic cells either kill the cells or the toxins are modified in a way that destroys toxicity. Consequently, plant toxin preparations typically have been purified in small quantities from plants in which the toxins are natively produced.

The availability of genes that encode desirable antibodies has caused a shift in focus away from antibody production in animals and animal cells, and toward the goal of obtaining active animal-derived antibodies from plants and plant cell cultures. It is the hope of workers in this field to increase the yield while decreasing the unit cost of purified antibody preparations.

Hiatt and co-workers developed transgenic tobacco plants that contained a DNA construct encoding either immunoglobulin light chain polypeptides or heavy chain polypeptides. Cross-pollination of transgenic tobacco plants yielded $F_1$ progeny plants that produced functional two-chain antibody molecules. The antibody constituted approximately 1% of total extractable protein. Hiatt and others have also obtained antibody production in a suspension culture of transgenic tobacco cells that contained a single vector encoding both a heavy chain gene and a light chain gene.

PCT patent application WO 91/02066 discloses the transformation of tobacco cells with a recombinant genetic construct encoding a single chain human serum albumin protein molecule fused to an N-terminal plant signal peptide. Human serum albumin was recovered from the medium in which the transgenic cells were cultured in suspension. The heterologous protein constituted approximately 0.02% of the extracellular protein. Expression of antibody-like single-chain variable region fragment ($sF_v$) proteins that bind antigens has been observed by Owen et al, *Bio/Technology*, 10:790 (1992) in transgenic tobacco plants at about 0.06–0.1% of total soluble protein.

Expression of novel fusion proteins, or immunofusion proteins, containing an antigen recognition function and an effector function not natively associated with the antigen recognition function has been described. Briefly, using molecular biological techniques, a DNA sequence encoding a desired effector function was introduced downstream from a sequence that encodes an $sF_v$ protein. Expression of these DNA constructs resulted in the synthesis of immunofusion proteins at low levels.

The art has expressed frustration at the inability to achieve high yields of the desired antibodies and protein toxins in a system from which the polypeptides can be readily purified. When a polypeptide is produced at a low level, either in absolute or relative terms, purification of the polypeptide from the plant or plant extract is more difficult.

BRIEF SUMMARY OF THE INVENTION

The present invention is summarized in that a method for producing a functional plant protein toxin or an immunologically active, conformationally intact mammalian antibody molecule in high yield from plant cell cultures includes transforming tobacco cells with a genetic construct that encodes a signal peptide that directs secretion of the protein toxin or antibody molecule, and recovering the desired protein toxin or antibody molecule produced by the cells. Preferably, the tobacco cells are tobacco suspension cells. Protein toxin or antibody can be recovered directly from the growth medium in which the transgenic suspension cells are cultured. These molecules retain their activity and can be used without renaturation or other efforts to restore native conformation and function.

The genetic construct encodes a protein that includes a signal peptide portion and either a plant toxin portion or a mammalian antibody portion that recognizes an antigen of interest. The signal peptide portion directs secretion of the protein from the host NT1 cells into the cell growth medium. The method disclosed allows production of immunologically active, conformationally intact mammalian antibody in higher yields than has been obtained by other methods known to the art. The method allows the production of relatively large quantities of polypeptide toxins in a heterologous expression system.

It is an object of the present invention to provide a method that permits the recovery of commercially useful quantities of immunologically active, conformationally intact mammalian antibody.

It is another object of the present invention to provide a method that permits the recovery of commercially useful quantities of plant protein toxins.

Other objects, advantages and features of the present invention will become apparent upon consideration of the following specification.

BRIEF DESCRIPTION OF THE SEVERAL VIEWS OF THE DRAWINGS

Not applicable.

DETAILED DESCRIPTION OF THE INVENTION

In the present invention, a genetic construct encoding protein that includes a signal peptide moiety and either a plant toxin or mammalian antibody portion is used to transform tobacco cells that can be grown in a suspension culture. Expression of the genetic construct occurs within transgenic tobacco cells. The protein encoded by the construct is secreted from the tobacco cells into the growth medium and may be recovered from the medium at concentrations between 25 and 200 mg protein/l of growth medium. The protein of interest can accumulate to concentrations of higher than 1% of extracellular protein. Preferably the accumulated protein is greater than 10% of the extracellular protein. The protein can accumulate to more than 50% or even more than 80% of the total extracellular protein.

In this patent application an "antibody" or "antibody molecule" is any single chain polypeptide molecule that includes an antigen recognition region. The antibody can include two variable regions joined together by a linker. The polypeptide can also include a region that has an effector function; this function can be one associated with naturally occurring antibodies or can be encoded by a gene not natively associated with the antigen recognition region The function could have cytotoxic or enzymatic activity, or any other desired activity. The term "antibody" is specifically intended to include the classes of antibody molecules known in the scientific literature as monoclonals, sFv (single chain variable region fragment) molecules, and SCA (single chain antibody) molecules.

As used here, "immunofusion" refers to an antibody or antibody molecule fused to another protein domain or segment which has a different origin or function than the native antibody molecule. An immunofusion is typically a fusion protein including an antigen recognition region from an antibody joined to a functional molecule, such as a toxin, which is directed to a site or target of interest by the antigen recognition segment.

Genetic construct

A genetic construct useful in the present invention includes, in operative 5' to 3' order, a promoter that promotes transcription in the host cells of plant origin, a signal sequence that encodes a signal peptide that directs secretion of a protein from the host cells, a DNA sequence that encodes a protein toxin or a secretable, conformationally active mammalian antibody molecule, and a transcription termination sequence functional in the host cells. The construct may also contain other advantageous features such as a selectable marker and a gene encoding a desired function.

The protein toxin can be any plant protein toxin. It may be full-length or truncated. The DNA fragment encoding the protein toxin can be any genomic or cloned DNA fragment, cDNA or a synthetic DNA that encodes a protein toxin of interest. The protein toxin can be any polypeptide that exhibits a pattern of toxicity that is comparable to that of the biologically active polypeptide isolated from the plant with which the toxin is natively associated.

The antibody encoded by the coding region may be full-length or truncated. The antibody may, but need not, encode the constant region that would be found in a naturally occurring full-length antibody molecule.

By "conformationally active" antibody is meant an antibody that retains antigen-recognition activity after purification. Activity includes any in vitro or in vivo immunological activity including activities useful in diagnostics and therapeutics. The DNA fragment encoding a secretable, conformationally active mammalian antibody can be any genomic or cloned DNA fragment, or cDNA, or synthetic DNA molecule capable of encoding an antigen recognition site of interest.

In nature, the antigen recognition site is encoded in part by a light chain and in part by a heavy chain, each of which includes variable and hypervariable regions which are together responsible for generating antibody diversity. It is well known that these regions of antibody light and heavy chain genes are prone to rearrangement and hypermutation during B-cell development. In addition, the ability of any mature light chain to combine with any mature heavy chain permits a virtually infinite number of antigen recognition sites to be formed, thereby facilitating the ability of the mammalian immune system to recognize with exquisite specificity an astounding number and variety of antigens.

It is possible using techniques known in the art to obtain germline or rearranged genetic material that encodes a desired antigen recognition site from a clonal population of cells. The art is well versed in techniques for generating clonal populations of B-cells or hybridoma cells that overproduce an antibody that recognizes a particular antigen. It is also intended that the antibody coding region for use in the present invention could also be provided by altering existing antibody genes using standard molecular biological techniques that result in the rearrangement, deletion, insertion, or substitution of one or more amino acids in the antibody produced.

The antibody coding region is preferably a genetically-engineered single chain fragment that encodes an antigen-binding variable region, or variants of such fragments. Such fragments, which include covalently-linked portions of both a heavy chain gene and a light chain gene, have been described by Bird et al., "Single-Chain Antigen-Binding Proteins," *Science* 242: 423–426 (1988) and by others. The heavy and light chain variable domains of single chain antibody fragments are joined together by a peptide linker. Genes encoding single chain antigen-binding fragments are typically incorporated in a genetic construct so as to encode an antigen-recognition portion of a fusion protein having a desired functional activity in a host cell. The desired functional activity is encoded by an effector gene fused in-frame to the gene encoding the antigen-recognition portion of the fusion protein. A wide variety of effector genes are known. The genes encoding the recognition and effector portions of the fusion protein can be complete coding regions obtained from wild-type genes, or may be mutant genes, relative to the naturally occurring forms of the genes. The genes utilized may be obtained from genomic DNA or from cDNA clones, may be synthesized in vitro or may be constructed in vitro from parts of other genes. Mutant genes may also be constructed to modify the nucleic acid and/or amino acid sequences as may be desired to modulate a particular function or activity encoded by the particular gene. Known techniques for introducing fine scale changes into known nucleic acid sequences include PCR mutagenesis.

Alternatively, the antibody molecule encoded by the genetic construct may be encoded as two separate DNA segments encoding separate portions of a single complete antibody molecule, such as a light chain gene and a heavy chain gene, under independent transcriptional control. In this case, the two protein chains encoded by the genetic construct combine in the cell to form a secretable functional antibody molecule having antigen recognition and/or effector functions.

The promoter for the protein toxin gene or the antibody-encoding gene(s) may be any promoter that is known to be active in plant host cells. Known plant promoters have generally been shown to work well in a variety of plant host cells. Thus, it is believed that any known plant promoter would be acceptable for use in the present invention. The promoter need not necessarily be derived from a plant gene, but may also be obtained from a virus or may be synthesized in vitro. The promoter may be inducible or constitutive. Examples of useful promoters are the Cauliflower Mosaic Virus 35S (CaMV 35S) and 19S (CaMV 19S) promoters and the nopaline synthase promoter (nos).

The terminator for the protein toxin gene and the antibody-encoding gene(s) may, likewise, be any sequence known to be active in plant cells that causes the addition of a poly A chain to mRNA. A suitable terminator is the nopaline synthase poly A addition sequence (nos polyA).

The signal sequence that directs secretion of the protein toxin or antibody from the host cell may be any DNA segment that confers upon the protein product the ability to be translocated across the cell membrane such that the product accumulates at high levels in the culture medium. If the signal sequence causes direct protein translocation, it is provided 5' to the toxin or antibody coding region. It is also envisioned that the protein may be secreted from the host by vacuolar translocation. In such a case, the signal sequence can be 5' or 3' to the region encoding the protein toxin or antibody. The tobacco 5' extensin signal sequence is a preferred signal sequence for use in tobacco cells since its behavior in such cells has been well characterized and since its nucleotide sequence has been published. De Loose, M. et al., *Gene*, 99:95–100 (1991). Sufficient quantities of the tobacco extensin signal sequence may be obtained for cloning into the DNA construct by subjecting tobacco genomic DNA to PCR amplification using primers that flank the signal sequence characterized by De Loose. Two preferred PCR-generated fragments are shown as SEQ ID: 1 and SEQ ID: 3, which encode 26 amino acids and 21 amino acids, respectively, from the 5' end of the tobacco extensin gene. When the 26 amino acid long signal sequence is placed 5' to an antibody or protein toxin coding region, the entire signal sequence is cleaved during peptide maturation precisely at the junction between the signal and the initial methionine residue of the antibody or protein toxin molecule. The 21 amino acid form of the signal sequence cleaves the mature peptide after the amino acid residue number 2 in the mature protein, thus generating a truncated form of the antibody or protein toxin. These two signal sequence fragments, which could alternatively be synthesized in vitro, can be provided conveniently as HindIII-NcoI fragments which make them amenable to insertion into the DNA construct.

The selectable marker if any, may be any gene that confers a selectable property upon the plant host cells. The marker is preferably a gene that confers antibiotic resistance on the otherwise antibiotic-sensitive host cells. Many such genes are known. An aphII gene conferring kanamycin resistance is a suitable selectable marker, although other genes that confer kanamycin resistance or resistance to another drug such as neomycin may be used. The selectable marker is preferably provided to the genetic construct as a single DNA fragment that includes a promoter functional in plant cells, a selectable marker gene, and a terminator sequence. The promoter and terminator may be any of those known to the art that allow expression of the selectable marker at a level sufficient to permit transformed cells to be distinguished from untransformed cells. The regulatory elements that direct expression of the antibody encoding gene or genes may also direct expression of the selectable marker.

In the accompanying examples, the exemplary genetic construct includes a gene encoding a tobacco 5' extensin or cotton signal sequence, and an sFv antigen recognition sequence under the transcriptional control of a CaMV 35S promoter and an nos poly A addition sequence.

Host cells

The genetic construct of the present invention may be used to transform any plant cell in which the construct can be expressed, and from which the expressed polypeptide can be secreted at concentrations higher than 25 mg/l of culture medium. Preferably the plant cells are cells that can grow in a suspension culture. Most preferably the plant cells are tobacco suspension cells. The use of tobacco suspension cells is advantageous because the desired proteins are secreted from tobacco suspension cells into the liquid medium, and the proteins constitute a large fraction of the extracellular proteins.

Alternatively, if desired, the transgenic suspension cells containing the desired construct may be used to form calli from which tobacco plants can be regenerated by methods known to one skilled in the art of plant micropropagation.

The tobacco cell line NT1 has been found to suitable for the practice of the present invention. These cells were originally developed from *Nicotiana tabacum* L.cv. bright yellow 2. The cell line NT1 is widely used and readily available. It is envisioned that any tobacco suspension cell can be used in the practice of the invention. However, one wishing to practice the present invention should be mindful that the origins of NT1 cells are obscure, the cell line is quite mutable, and the cell line appears to change in response to culture conditions. A culture of NT1 cells used in the examples below has been deposited with the American Type Culture Collection to enable others to practice the present invention. The NT1 culture was assigned ATCC No. 74840 following its deposit on Jul. 22, 1994.

DNA transformation

A variety of systems have been used by the present inventors to introduce the DNA constructs described into plant cells. The cells may be transformed with the DNA constructs by an Agrobacterium-mediated method, by an accelerated particle delivery method, a cell fusion method, an electroporation method, or by any other method for delivering DNA in an expressible form into a host cell.

A preferred method of introducing DNA into cells is accelerated particle delivery. The method published by Russell, J. et al., *In Vitro Cell. Dev. Biol.*, 28P:97–105 (1992) and the method of An, G., *Plant Physiol.*, 79:568–570 (1985) have been successfully used to deliver genetic constructs described herein into tobacco suspension cells. The transfer protocol is detailed in the Examples. It is understood that modifications of this protocol are within the ability of one skilled in the art.

Protein purification

Depending upon the level of purity desired, any known protein purification technique may be used to purify secreted proteins of interest from the spent culture medium. Such techniques may include filtration, ultrafiltration, precipitation, affinity chromatography, ion exchange chromatography, hydrophobic interaction chromatography, and any other method useful in the purification of antibodies or protein toxins.

However, because the secreted antibody or protein toxin typically accounts for such a high proportion of the total extracellular protein (as high as 80%) the protein may, for certain applications, be used without further purification from other proteins. The percent specific yield, and the concentration of desired protein, in this system are markedly higher than those reported in the art where the desired protein has typically been reported at much less than 1% of soluble protein in the culture media.

After the protein has been isolated and, if necessary, purified, it may be used in the same ways as proteins isolated from the organism with which they are natively associated. The antibody may be used in any immunological assay, such as ELISA or Western Blot, or immunological therapy, such as anti-tumor treatments. Thus the present invention provides a desirable high-yield source of animal antibodies without using animals or animal cell cultures. A purified plant toxin may be used as a therapeutic agent. For example, the plant toxin may be used as a cytotoxin directed against specific cancer cells by covalently linking the toxin to an antibody that recognizes a particular antigenic deterimant associated with the cancer cell.

Using the method of this invention, it is possible to isolate between about 25 and 200 mg of a mammalian antibody or plant protein toxin are isolated per liter of a transgenic tobacco cell suspension culture. The heterologous proteins produced by this method can account for as much as 80% of the protein in the culture medium.

The examples below serve to further clarify the invention and are intended to be purely illustrative of the method of the present invention.

EXAMPLES

Signal Sequences 1. ext26. A 26 amino acid long signal sequence from the 5' end of the tobacco extensin gene was obtained by PCR from tobacco genomic DNA. The tobacco extensin gene was described by De Loose, et al., *Gene,* 99:95–100 (1991), although this paper did not define the extent of the signal sequence. The PCR product was cloned as a HindIII-NcoI fragment and sequenced. The DNA sequence of ext26 is shown as SEQ ID NO:1. The 26 amino acid signal sequence is shown in SEQ ID NO: 2. The inventors herein disclose that when incorporated in-frame into an expressible genetic construct with an sFv gene, ext26 encodes a signal peptide that is cleaved from the mature protein precisely at the junction between the signal peptide and the ATG start codon of the sFv gene.

2. ext21. A second signal sequence from the tobacco extensin gene that encodes a 21 amino acid long signal peptide was also cloned on a HindIII-NcoI fragment for use in other plasmids. The DNA sequence of ext21 is shown as SEQ ID NO:3. The 21 amino acid sequence is shown in SEQ ID NO:4. When incorporated in-frame into an expressible genetic construct with an L6 sFv gene, ext21 encodes a signal peptide that is cleaved from the mature protein after amino acid number 23. Thus a 2 amino acid deletion from the amino terminus of the L6 sFv protein results. It is believed, therefore, that the length of the signal peptide is important for obtaining the desired mature protein.

3. GK12. A signal peptide from a cotton gene was also tested. The DNA encoding the cotton signal peptide GK12 was obtained from a cDNA clone that appears to encode a protein homologous to a class of plant peptide called Lipid Transfer Protein (LTP). The DNA sequence encoding the GK12 signal peptide is shown at SEQ ID NO: 5.

Plant Protein Toxin Genes

The plant toxin BD1 is a 247 amino residue protein with a molecular weight of 28 kDa. The BD1 toxin was first isolated from the roots of *Brionia dioica.* It effects its toxicity through inhibition of protein synthesis. A rBD1 expression vector, designated pSE13.0 (Siegall, et al. *Bioconj. Chem.* 5:423–429, 1994) was used to construct the BD1 encoding DNA sequence used in the present invention. The DNA sequence encoding amino acids 1–247 of BD1 was obtained by digestion of pSE13.0 with NcoI and EcoRI. This fragment was used in the construction of an expression vector designated pWRG5074, described below. The DNA sequence of this fragment is shown in SEQ ID NO:6 and the amino acid sequence is shown in SEQ ID NO:7.

Single chain antibody genes

L6 anti-tumor antibody binds to a cell surface antigen expressed by many human carcinomas. Two DNA sequences that encode the L6 anti-tumor antibody polypeptides L6 sFv and L6 cys sFv were used in the present invention. Both L6 sFv and L6 cys sFv recognize human carcinomas. The DNA sequence that encodes L6 sFv is shown in SEQ ID NO:8, and the corresponding amino acid sequence is shown in SEQ ID NO:9.

The DNA sequences encoding L6sFv and L6 cys sFv differ from each other only at nucleotides 145–147. As can be seen in SEQ ID NO:8, nucleotides 145–147 of the L6 sFv sequence comprise an AAA codon specifying a lysine residue at amino acid position number 49 of the polypeptide gene product (SEQ ID NO:9). In contrast, L6 cys sFv has a TGT codon specifying a cysteine residue amino acid position number 49. The DNA sequence encoding L6 cys sFv was obtained by in vitro mutagenesis of the L6 sFv gene. The substitution of a cysteine for the lysine residue at amino acid 49 allows the chemical coupling of therapeutic moieties to the L6 antibody at the cysteine residue.

The L6 sFv and the L6 cys sFv DNA coding regions produced similar results in the examples below. The majority of the L6-related data were collected using L6 cys sFv. Polyclonal antisera that recognize the L6 antibody as well as anti-idiotype antibodies that recognize L6 sFv and L6 cys sFv only in their native conformation were described by Hellstrom, et al., "Epitope Mapping and Use of Anti-Idiotypic Antibodies to the L6 Monoclonal Anticarcinoma Antibody," *Cancer Research,* 50:2449–2454 (1990).

A construct containing an anti-TAC sFv single chain antibody gene, the product of which recognizes a portion of the IL2 receptor, was also used to transform tobacco suspension cells. The anti-TAC sFv was derived from a construct encoding an sFv-Pseudomonas exotoxin protein described in *Nature* 339:394–397 (1989) and in *J. Biol. Chem.,* 265:15198–15202 (1990). The Pseudomonas exotoxin portion of the gene fusion was deleted and appropriate transcription signals were added to allow expression of the sFv alone. The anti-TAC sFv coding sequence is shown in SEQ ID NO:10. The protein encoded by the gene is shown in SEQ ID NO:11. The anti-TAC sFv produced by expression of the construct is able to bind to the IL2 receptor.

A construct containing a G28.5 sVf single chain antibody gene, whose product recognizes CD40 cell surface protein, was also used to transform tobacco suspension cells. The construct, designated pWRG5280, contains the G28.5sVf gene from pSE51. Expression of functional G28.5 sFv antibody was obtained in tobacco suspension cells. The coding region of the G28.5 sFv DNA sequence is shown in SEQ ID NO:12, and the deduced amino acid sequence is shown in SEQ ID NO:13.

A genetic construct containing a DNA sequence that encodes a single chain antibody comprising a fusion protein was also used to transform tobacco cells grown in suspension cell cultures. The single chain antibody contains the recognition portion of the G28.5 sVf antibody and the protein toxin BD1. This construct was prepared by PCR amplification of the G28.5 gene from pSE51, adding a 5' NcoI site and an EcoRI site after the stop codon. Similarly, PCR amplification of the BD1 gene from pSE13.0 was performed in such a manner as to include a 5' NdeI site and a 3' NcoI site. The two PCR fragments were then digested as appropriate and ligated into pSE13.0 which had been digested with NdeI and EcoRI, yielding a plasmid designated pSE151, containing a BD1-G28.5 fusion gene. This fusion gene was then amplified by PCR introducing a 5' NcoI and a 3' SmaI site and the PCR product was transferred into a plant expression vector pWRG2482, to make a plasmid designated pWRG5292. A selectable marker cassette was added to the plasmid to make pWRG5293. The DNA and deduced amino acid sequences of the BD1-G28.5 fusion gene are shown in SEQ ID NO:14 and SEQ ID NO:15, respectively.

Plasmids

All plasmids described below were constructed using standard genetic engineering techniques using pUC19 derivatives. Each plasmid includes an aphII selectable marker gene in an expressible cassette under the transcriptional control of the nos promoter and soybean poly A addition sequence.

1. pWRG2509. This plasmid includes (5' to 3') a Cauliflower Mosaic Virus 35S promoter (CaMV 35S) that provides transcriptional control of downstream protein-encoding portions of the molecule, and DNA encoding the L6 cys sFv single chain anti-tumor antibody.

2. pWRG2510. This plasmid includes (5' to 3') the CaMV 35S promoter, a DNA sequence encoding the ext26 signal peptide, and a DNA sequence encoding the L6 cys sFv single chain anti-tumor antibody fused in-frame to the ext26 DNA.

3. pWRG2618. This plasmid includes (5' to 3') the CaMV 35S promoter, a DNA sequence encoding the ext21 signal peptide, and a DNA sequence encoding the L6 cys sFv single chain anti-tumor antibody fused in-frame to the ext21.

4. pWRG2778. This plasmid includes (5' to 3') the CaMV 35S promoter, a DNA sequence encoding the cotton GK12 signal peptide, and a DNA sequence encoding the L6 cys sFv single chain anti-tumor antibody fused in-frame to the GK12 DNA.

5. pWRG2835. This plasmid includes (5' to 3') the CaMV 35S promoter, a DNA sequence encoding the ext26 signal peptide, and a DNA sequence encoding the anti-Tac sFv DNA fused in-frame to the ext26 DNA.

6. pWRG5074. This plasmid includes (5' to 3') the CaMV 35S promoter, a DNA sequence encoding an extensin signal peptide, and a DNA sequence encoding plant toxin BD1 fused in-frame to the extensin-encoding DNA.

7. pWRG5280. This plasmid includes (5' to 3') an extensin promoter, a DNA sequence encoding an extensin signal peptide, and a DNA sequence encoding the G28.5 sFv single chain anti-tumor antibody fused in-frame to the extensin-encoding DNA.

8. pWRG5293 This plasmid includes (5' to 3') the CaMV 35S promoter, a DNA sequence encoding an extensin signal peptide, and a DNA sequence encoding a polypeptide, consisting of the BD1 toxin and the G28.5 sFv single chain anti-tumor antibody, fused in-frame to the extensin-encoding DNA.

Transformation of NT1 Cells Using Microparticle Bombardment

Tobacco NT1 cells were grown in suspension culture according to the procedure described in Russell, J., et al., *In Vitro Cell. Dev. Biol.,* 28P:97–105 (1992) and An, G., *Plant Physiol.,*79:568–570 (1985). Prior to bombardment, fresh tobacco suspension media (TSM) was inoculated using NT1 cells in suspension culture, and the culture was allowed to grow four days to early log phase. TSM contains, per liter, 4.31 g of M.S. salts, 5.0 ml of WPM vitamins, 30 g of sucrose, 0.2 mg of 2,4-D (dissolved in KOH before adding). The medium is adjusted to pH 5.8 prior to autoclaving. Early log phase cells were plated onto 15 mm target disks on tobacco culture medium (TCM) containing 0.3M osmoticum and held for one hour prior to bombardment. The solid medium TCM consists of TSM plus 1.6 g/l Gelrite (Scott Laboratories, West Warwick, R.I.).

Efficient transformation of NT1 cells was obtained as follows. The DNA construct was delivered into the plated NT1 cells using a spark discharge particle acceleration device as described in U.S. Pat. No. 5,120,657, which is incorporated herein by reference. Delivery voltages ranged from 12–14 kV.

Following transformation of the NT1 cells, the disks containing the cells were held in the dark for one day. During this period, the discs were transferred twice at regular intervals to solid medium containing progressively lower concentrations of osmoticum. The cells were then transferred to TCM containing 350 mg kanamycin sulphate/liter and grown for 3–12 weeks, with weekly transfers to fresh media. After 3–6 weeks of growth on solid medium, kanamycin resistant calli of transgenic NT1 cells may be used to start a suspension culture in TSM containing 350 mg kanamycin sulphate/liter.

Expression of the genetic constructs in the transgenic plant cells was evaluated. Total protein present in the spent media was measured by the Biorad protein determination assay. The secreted peptides of interest were purified from the media using different purification procedures and assayed by various means. At each step of the purification, proteins contained within aliquots of various fractions were subjected to polyacrylamide gel electrophoresis (PAGE) and stained with coomassie dye. To allow identification and quantitation of the polypeptides, size standards and a range of samples containing known amounts of protein were also included on the PAGE gels.

The expression and secretion of anti-TAC sFv was confirmed by amino acid sequencing of the N-terminal region of the antibody. The sequencing data indicated that the sequenced region of the protein had the proper sequence, and that the polypeptide had been properly processed with respect to cleavage of the signal peptide. The L6 cys sFv was identified and quantified by ELISA using anti-idiotype antibody 13B, which is specific for L6 antibody in its native conformation. The secreted L6 cys sFv was found to constitute as much as 80% of total extracellular protein.

| DNA construct | Expression |
|---|---|
| pWRG2509 | <1 mg/l |
| pWRG2510 | 200 mg/l |
| pWRG2618 | 25 mg/l |
| pWRG2778 | 45 mg/l |
| pWRG2835 | 100 mg/l |
| pWRG5074 | 80 mg/l |
| pWRG5280 | 40 mg/l |
| pWRG5293 | 0.1 mg/l |

These results demonstrate high yields of polypeptides such as mammalian antibodies or plant toxins using transgenic tobacco suspension cells when the DNA encoding the polypeptide is genetically engineered to contain a signal sequence. These polypeptides comprise a relatively large percentage of total extracellular protein. A suitable signal sequence is required for the practice of this invention. However, the signal sequence can be obtained from the tobacco extensin gene, a cotton gene, or, by extension, any other plant signal sequence that causes secretion of proteins from the transgenic cells. It has also been demonstrated that high protein yields can be obtained using various coding regions of the extensin gene. Therefore, the invention is not limited to the particular genes or signal sequences tested.

It is to be understood that the present invention is not limited to the particular embodiments disclosed in this application, but embraces all such modified forms thereof as come within the scope of the following claims.

What is claimed is:

1. A method for obtaining secretable plant protein toxins from plant cells, comprising the steps of:

providing a DNA construct comprising a selectable marker and, in 5' to 3' order, a promoter that promotes transcription in tobacco cells in cell culture, a plant sequence that encodes a peptide that directs secretion of a protein from the tobacco cells, a DNA sequence that encodes a secretable heterologous plant protein toxin, and a transcription terminator functional in tobacco cells;

transforming tobacco suspension cells with the DNA construct;

selecting for transgenic tobacco cells in which the selectable marker gene of the DNA construct is expressed;

culturing the transgenic tobacco cells in a liquid suspension culture under condition such that the secretable protein toxin encoded by the DNA construct accumulates in the liquid culture to a concentration of greater than 25 mg/l, the accumulated mammalian single chain antibody comprising more than 10% of the total secreted protein in the medium; and isolating the accumulated protein toxin away from the tobacco cells.

2. A method as claimed in claim 1 wherein the signal sequence is a tobacco extensin signal sequence.

3. A method as claimed in claim 2 wherein the signal sequence is 26 amino acids long.

4. A method as claimed in claim 2 wherein the signal sequence is 21 amino acids long.

5. A method as claimed in claim 1 wherein the signal sequence is a cotton GK12 signal sequence.

6. A method as claimed in claim 1 wherein the protein toxin is BD1.

7. A method as claimed in claim 1 wherein the promoter is a Cauliflower Mosaic Virus 35S promoter, the signal sequence is a 26 amino acid long signal sequence from a tobacco extensin gene, and the plant protein toxin is BD1.

8. A method as claimed in claim 1 wherein the transforming step comprises the steps of coating the DNA construct onto carrier particles, and accelerating the coated particles toward the tobacco cells such that some of the coated particles are delivered into some of the cells.

9. A method as claimed in claim 1 wherein the tobacco cells are NT1 cells.

10. A method for preparing plant protein toxin, comprising the steps of:

transforming NT1 tobacco suspension cells with a DNA construct, the DNA construct comprising an expressible selectable marker gene and, in 5' to 3' order, a Cauliflower Mosaic Virus 35S promoter, a signal sequence selected from the group consisting of a 26 amino acid long signal sequence from a tobacco extensin gene, a 21 amino acid long signal sequence from the tobacco extensin gene, and a signal sequence from a cotton GK12 cDNA clone, a coding region encoding a heterologous plant protein toxin, and a transcription terminator functional in the NT1 cells;

selecting for cells expressing the selectable marker gene;

culturing the transgenic tobacco cells in a liquid medium under conditions such that the single chain mammalian antibody encoded by the DNA construct to accumulate in the liquid to a concentration over 25 mg/l, the accumulated mammalian single chain antibody comprising more than 10% of the total secreted protein in the medium; and isolating the accumulated single chain mammalian antibody away from the NT1 cells.

11. A method as claimed in claim 10 wherein the transforming step comprises the steps of coating the DNA construct onto carrier particles, and accelerating the coated particles toward the tobacco cells such that some of the coated particles are delivered into some of the cells.

* * * * *

UNITED STATES PATENT AND TRADEMARK OFFICE
CERTIFICATE OF CORRECTION

PATENT NO. : 6,140,075
DATED : October 31, 2000
INVENTOR(S) : David Russell et al.

It is certified that error appears in the above-identified patent and that said Letters Patent is hereby corrected as shown below:

Column 35, claim 1,
Lines 19 to 20, change "mammalian single chain anitbody" to -- plant protein toxin --.

Column 36, claim 10,
Lines 16 to 17, change "single chain mammalian antibody" to -- plant protein toxin --.
Lines 19, change "mammalian single change antibody" to -- plant protein toxin --.
Lines 22 to 23, change "single chain mammalian antibody" to -- plant protein toxin --.

Signed and Sealed this

Fifth Day of March, 2002

*Attest:*

JAMES E. ROGAN
*Attesting Officer*     *Director of the United States Patent and Trademark Office*